(12) United States Patent
Woodcock et al.

(10) Patent No.: US 10,492,334 B2
(45) Date of Patent: Nov. 26, 2019

(54) METHODS, SYSTEMS, AND ASSEMBLIES FOR COOLING AN ELECTRONIC COMPONENT

(71) Applicant: Rensselaer Polytechnic Institute, Troy, NY (US)

(72) Inventors: Corey Christopher Woodcock, Saratoga Springs, NY (US); Joel L. Plawsky, Albany, NY (US); Yoav Peles, Orlando, FL (US); Xiangfei Yu, Troy, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 0 days.

(21) Appl. No.: 15/869,173

(22) Filed: Jan. 12, 2018

(65) Prior Publication Data

US 2018/0199469 A1    Jul. 12, 2018

Related U.S. Application Data

(60) Provisional application No. 62/613,343, filed on Jan. 3, 2018, provisional application No. 62/445,296, filed on Jan. 12, 2017.

(51) Int. Cl.
*H05K 7/20* (2006.01)
*H01L 23/473* (2006.01)
(Continued)

(52) U.S. Cl.
CPC ....... *H05K 7/20436* (2013.01); *H01L 23/473* (2013.01); *H05K 7/20272* (2013.01);
(Continued)

(58) Field of Classification Search
CPC .......... H05K 7/20436; H05K 7/20409; H05K 7/20272; H05K 7/20254; H05K 7/20509;
(Continued)

(56) References Cited

U.S. PATENT DOCUMENTS 6,422,307 B1    7/2002  Bhatti et al.
6,457,515 B1   10/2002  Vafai et al.
(Continued)

FOREIGN PATENT DOCUMENTS

CN      102856609 A    1/2013
CN      103487459 A    1/2014
(Continued)

OTHER PUBLICATIONS

Milnes P. David, et al., Hydraulic and thermal characteristics of a vapor venting two-phase microchannel heat exchanger, International Journal of Heat and Mass Transfer, Aug. 18, 2011, pp. 5504-5516.
(Continued)

*Primary Examiner* — Anatoly Vortman
*Assistant Examiner* — Stephen S Sul
(74) *Attorney, Agent, or Firm* — Murtha Cullina LLP (57) ABSTRACT

Methods, systems, and assemblies for cooling an electronic component are disclosed. A heat sink assembly includes first and second substrates. The first substrate is in thermal contact with the electronic component. A primary channel is formed in the second surface of the first substrate. The primary channel is configured to direct cooling fluid for cooling the electronic component. An array of primary cooling fluid fins is positioned within the primary channel. The array of primary cooling fluid fins includes upstream solid fins and downstream open fins each having an upstream opening and downstream sidewalls. The secondary channel is formed within the second surface of the second substrate and is configured to direct partially heated cooling fluid away from the electronic component. An array of secondary cooling fluid fins is positioned within the secondary channel downstream. An enclosing layer seals the secondary channel.

9 Claims, 5 Drawing Sheets

(51) Int. Cl.
*C09K 5/10* (2006.01)
*C07C 43/12* (2006.01)
*H01L 23/367* (2006.01)

(52) U.S. Cl.
CPC ....... *H05K 7/20409* (2013.01); *C07C 43/126* (2013.01); *C09K 5/10* (2013.01); *H01L 23/3677* (2013.01)

(58) Field of Classification Search
CPC ... H01L 23/473; H01L 23/3677; H01L 23/46; H01L 21/4882; C09K 5/10; C07C 43/126
USPC ....... 361/679.47, 679.54, 702, 709, 710, 711
See application file for complete search history.

(56) References Cited

U.S. PATENT DOCUMENTS

| | | | |
|---|---|---|---|
| 6,479,326 | B1 | 11/2002 | Corisis et al. |
| 7,035,104 | B2 | 4/2006 | Meyer |
| 7,104,312 | B2* | 9/2006 | Goodson ............... F04B 19/006 165/104.33 |
| 7,561,425 | B2 | 7/2009 | Mindock et al. |
| 7,763,973 | B1 | 7/2010 | Bratkovski et al. |
| 7,836,706 | B2 | 11/2010 | Tilton et al. |
| 8,110,415 | B2 | 2/2012 | Knickerbocker et al. |
| 8,485,247 | B2* | 7/2013 | Lavric ................... B01J 19/0093 165/166 |
| 8,686,556 | B2 | 4/2014 | Clark et al. |
| 2006/0002087 | A1* | 1/2006 | Bezama ..................... F28F 3/12 361/699 |
| 2006/0002088 | A1* | 1/2006 | Bezama ..................... F28F 3/04 361/702 |
| 2006/0227827 | A1* | 10/2006 | Kawanishi .......... H01S 5/02423 372/36 |
| 2006/0231237 | A1 | 10/2006 | Dangelo |
| 2009/0315173 | A1* | 12/2009 | Kempers ................ B21D 53/02 257/713 |
| 2012/0008655 | A1* | 1/2012 | Niwa .................. H01L 21/4882 372/36 |
| 2012/0170222 | A1* | 7/2012 | Dede ....................... F28F 3/083 361/702 |
| 2012/0212907 | A1* | 8/2012 | Dede .................. H01L 23/4735 361/702 |
| 2013/0070420 | A1 | 3/2013 | Campbell et al. |
| 2014/0231055 | A1* | 8/2014 | Schalansky ............. F28F 3/086 165/166 |
| 2015/0311137 | A1 | 10/2015 | Oganesian |
| 2017/0054265 | A1 | 2/2017 | Downing |
| 2017/0092565 | A1* | 3/2017 | Chen ..................... H01L 23/473 |

FOREIGN PATENT DOCUMENTS

| | | |
|---|---|---|
| CN | 104347546 A | 2/2015 |
| TW | 201625891 A | 7/2016 |
| WO | 2016194158 A1 | 12/2016 |
| WO | 2017083383 A1 | 5/2017 |

OTHER PUBLICATIONS

Milnes P. David, et al., Vapor-Venting, Micromachined Heat Exchanger for Electronics Cooling, Proceedings of IMECE 2007-42553, Nov. 11-15, 2007, pp. 1-10.
Yoav Peles et al., Forced convective heat transfer across a pin fin micro heat sink, International Journal of Heat and Mass Transfer, Aug. 2005, pp. 5504-5516.
Sheng-Chih Lin, et al., Cool Chips: Opportunities and Implications for Power and Thermal Management, IEEE Transactions on Electron Devices, vol. 55, No. 1, Jan. 2008, pp. 245-255.
Avram Bar-Cohen, et al., Direct Liquid Cooling of High Flux Micro and Nano Electronic Components, Article in Proceedings of the IEEE, Sep. 2006, pp. 1549-1570.
Hyung Beom Jang, et al., The Impact of Liquid Cooling on 3D Multi-Core Processors, Conference Paper, Nov. 2009, pp. 472-478.
Critical Power and Cooling Market by Type, End Use & by Region—Global Forecast to 2021 MarketsAndMarkets Mar. 2017; www.marketsandmarkets.com/Market-Reports/critical-power-and-cooling-market-145371177.
Thermal Management Market by Material Type—2022 MarketsAndMarkets May 2017; www.marketsandmarkets.com/Market-Reports/thermal-management-market-155049228.
Global Thermal Management Technologies Market Analysis & Trends—Industry Forecast to 2025 ResearchAndMarkets Sep. 2016, www.researchandmarkets.com/reports/3861658/global-thermal-management-technologies-market.
The Market for Thermal Management Technologies: SMC024K | BCC Research BCC Research Mar. 2016, www.bccresearch.com/market-research/semiconductor-manufacturing/the-market-for-thermal-management-technologies-report-smc024k.
Paisarn Naphon, et al., Nanofluid jet impingement heat transfer characteristics in the rectangular mini-fin heat sink, Journal of Engineering Physics and Thermophysics, Nov. 2012, vol. 85, Issue 6, Abstract.

* cited by examiner

METHODS, SYSTEMS, AND ASSEMBLIES FOR COOLING AN ELECTRONIC COMPONENT

CROSS REFERENCE TO RELATED APPLICATION(S)

This application claims the benefit of U.S. Application Nos. 62/445,296, filed Jan. 12, 2017, and 62/613,343, filed Jan. 3, 2018, which are incorporated by reference as if disclosed herein in their entirety.

STATEMENT REGARDING FEDERALLY SPONSORED RESEARCH OR DEVELOPMENT

This invention was made with government support under grant no. HR0011-13-2-0013 awarded by the Defense Advanced Research Projects Agency. The government has certain rights in the invention.

BACKGROUND

Power densities in electrical components have reached unprecedented levels as processing power increases in ever decreasing package sizes. In some cases, heat fluxes from component surfaces are so large that the heat loads cannot be mitigated through conventional cooling technology. These heat fluxes can extend well beyond 1 kW/cm$^2$. Overheating in electrical components, such as integrated circuits, can result in excess signal noise, reduced component operational lifetimes, and mechanical failures.

Thus advanced embedded or integrated heat sinks are being developed for the newest generation of computing, laser, radar, and diode systems, amongst others, to handle heat fluxes in excess of 1 kW/cm$^2$. In such embedded or integrated cooling systems, a cooling fluid flows around, between, and/or through positions of the electrical component to provide cooling at the heat source. Strong initiatives have been put in place recently by both industry and government bodies to develop these advanced heat sinks, the Defense Advanced Research Projects Agency (DARPA) Intrachip/Interchip Enhanced Cooling Fundamentals (ICE-Cool Fundamentals) program being an example.

SUMMARY

Some embodiments of the disclosed subject matter include a heat sink assembly for cooling an electronic component including the following: a first substrate including first and second surfaces, the first surface being in thermal contact with the electronic component; a primary channel formed in the second surface of the first substrate, the primary channel being configured to direct cooling fluid for cooling the electronic component; an array of primary cooling fluid fins positioned within the primary channel, the array of primary cooling fluid fins including upstream solid fins and downstream open fins each including an upstream opening and downstream sidewalls; a second substrate including first and second surfaces with the first surface of the second substrate positioned in thermal contact with the second surface of the first substrate, the second substrate including cooling fluid conduits having upstream and downstream ends and each being formed through the second substrate from the upstream end at the first surface to the downstream end at the second surface; a secondary channel formed within the second surface of the second substrate, the secondary channel being configured to direct partially heated cooling fluid away from the electronic component; an array of secondary cooling fluid fins positioned within the secondary channel downstream, each being positioned downstream of one of the fluid conduits; an enclosing layer for sealing the secondary channel; a cooling fluid inlet formed in the primary channel; and a cooling fluid outlet formed in at least one of the enclosing layer and the secondary channel.

Some embodiments of the disclosed subject matter include a system for cooling an electronic component that includes the following: a cooling fluid source; a heat sink assembly as described above positioned in thermal contact with the electronic component, the heat sink assembly including a cooling fluid inlet and a cooling fluid outlet; conduits for joining the cooling fluid inlet and outlet in fluid communication with the cooling fluid source; and a pump positioned between the cooling fluid source and the cooling fluid inlet of the heat sink assembly, the pump being configured to draw a cooling fluid from the cooling fluid source and pump it into the heat sink assembly via the cooling fluid inlet and through the heat sink assembly to the cooling fluid outlet.

Some embodiments of the disclosed subject matter include a method of cooling an electronic component that includes the following: positioning a heat sink assembly including a bi-directional cooling fluid flow path in thermal communication with the electronic component; providing a supply of a cooling fluid having a first temperature; directing the cooling fluid having a first temperature through the heat sink assembly in a first direction that is substantially parallel to a plane defined by a surface of the electronic component in thermal communication with the heat sink assembly so that the cooling fluid having a first temperature is in thermal communication with a portion of the heat sink assembly in thermal communication with the electronic component; directing the cooling fluid having a second temperature that is greater than the first temperature in a second direction that is substantially perpendicular to the plane defined by the surface of the electronic component in thermal communication with the heat sink assembly; directing the cooling fluid having a second temperature in a third direction that is substantially parallel to the first direction; and continuously repeating prior steps while the electronic component is energized.

BRIEF DESCRIPTION OF THE DRAWINGS

The drawings show embodiments of the disclosed subject matter for the purpose of illustrating the invention. However, it should be understood that the present application is not limited to the precise arrangements and instrumentalities shown in the drawings, wherein.

DETAILED DESCRIPTION

Figure 1:
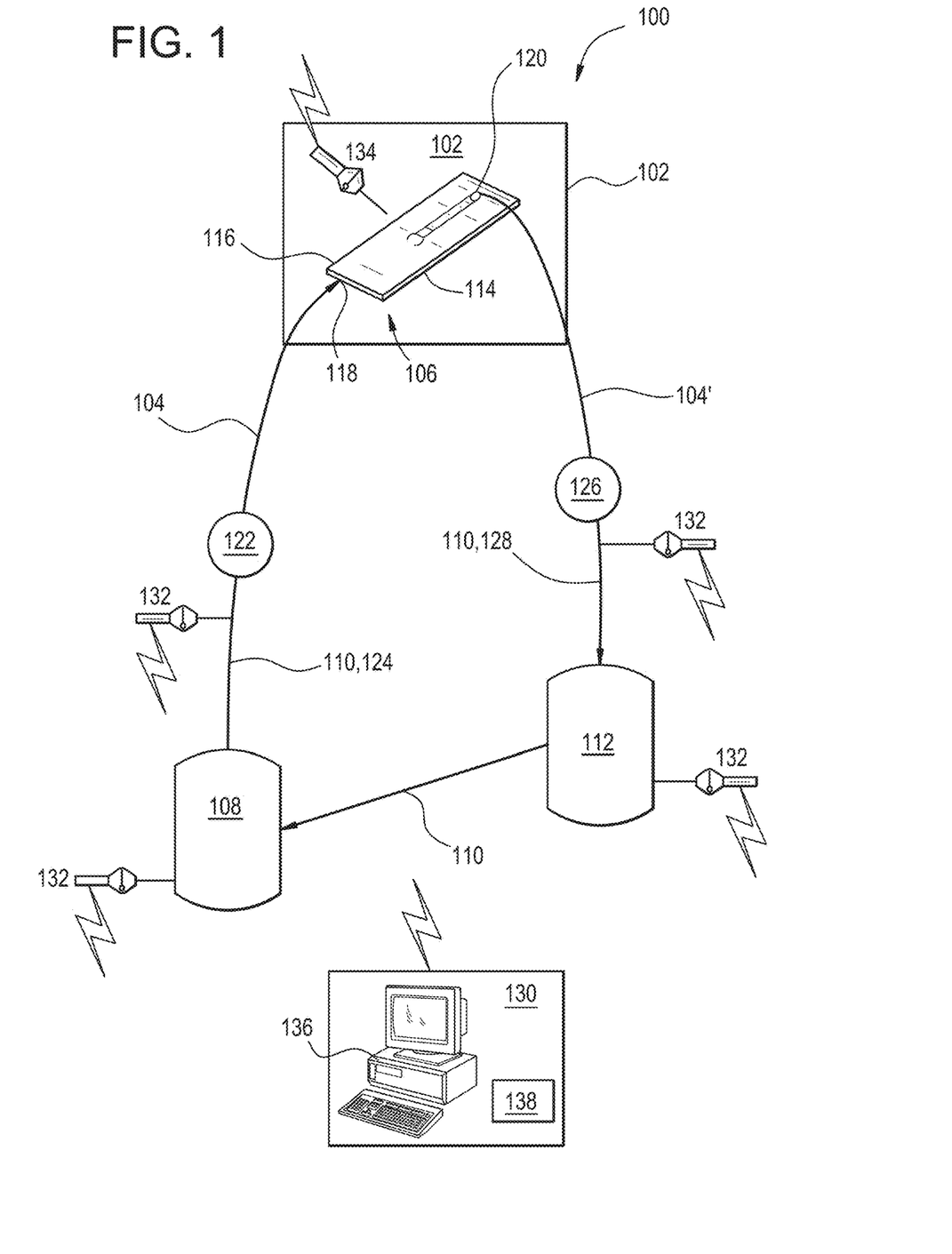
FIG. 1 is a schematic diagram of systems and methods according to some embodiments of the disclosed subject matter.
Figure 2:
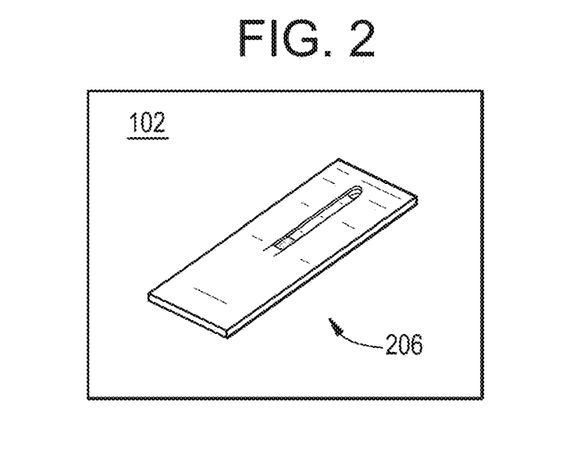
FIG. 2 is an enlarged partial isometric view of a fluid cooling assembly positioned on an electronic component according to some embodiments of the disclosed subject matter.

Referring now to FIG. 1, some embodiments of the disclosed subject matter include a system 100 for cooling an electronic component 102 that circulates a cooling fluid 104 through a heat sink assembly 106 that is in thermal contact with the electronic component. In some embodiments, system 100 is stamped, machined, molded, or 3D-printed from one or more materials as discussed in greater detail below.

Cooling fluid 104 is supplied from a cooling fluid source 108 to heat sink assembly 106 via conduits 110. In some embodiments, cooling fluid 104 is any fluid or gas suitable for extracting heat from heat sink assembly 106. In some embodiments, cooling fluid 104 is a hydrofluoroether. Some embodiments include a second cooling fluid source 112 in fluid communication with cooling fluid source 108 and/or heat sink assembly 106.

Heat sink assembly 106, which is described in further detail below, includes first and second substrates 114 and 116, respectively, which are joined with one another via known bonding methods, including but not limited to, direct fusion, adhesive bonding, welding, etc. Heat sink assembly 106 includes at least one cooling fluid inlet 118 and at least one cooling fluid outlet 120, both of which are joined with cooling fluid source 108 and/or cooling fluid source 112 via conduits 110.

System 100 includes a pump 122 positioned between cooling fluid source 108 and cooling fluid inlet 118 of heat sink assembly 106. Pump 122 is positioned and configured, e.g., sized, etc., to draw cooling fluid 104 from cooling fluid source 108 via one 124 of conduits 110 and pump it into the heat sink assembly via cooling fluid inlet 118 and through heat sink assembly 106 to the cooling fluid outlet 120. As it is at least partially heated, i.e., it has a temperature that is higher than when it first entered heat sink assembly 106, cooling fluid 104 is transformed so as to be identified as cooling fluid 104' when adjacent cooling fluid outlet 120. In some embodiments, a second pump 126 is positioned and configured, e.g., sized, etc., to draw cooling fluid 104' from heat sink assembly 106 via cooling fluid outlet 120 via one 128 of conduits 110 and to either a cooling tank (not shown), to second cooling fluid source 112, or to cooling fluid source 108.

In some embodiments, system 100 includes a control module 130 that has temperature sensors 132 and 134 for determining temperatures of cooling fluid 104 and 104' in cooling fluid supply 108 and conduits 110 and a temperature of a surface of electronic component 102 adjacent heat sink assembly 106. Control module 130 includes a computer device 136 and one or more software programs 138 for processing temperature data, e.g., from temperature sensors 132 and/or 134. In some embodiments, the temperature data is used to determine whether pumps 122 and 126 are activated and to what extent, e.g., at what flow rate. In some embodiments, control module 130 is connected with all of the components in system 100 and controls the components either manually or automatically depending on sensor data. In some embodiments, other sensors for measuring other characteristics of fluid flow, e.g., pressure, velocity, etc., are included. Sensors included with control module 130 are wired or wireless depending on the particular application.

Referring now to FIGS. 2-8, some embodiments include a heat sink assembly 206 (analogous to heat sink assembly 106 above), for cooling electronic component 102. Heat sink assembly 206 includes first and second substrates 208 and 210, respectively, which form an at least bi-directional and bi-axial pathway 212 through which cooling fluids 104 and 104' flow. In some embodiments, heat sink assembly 206 includes two or more first substrates 208.

Figure 4:
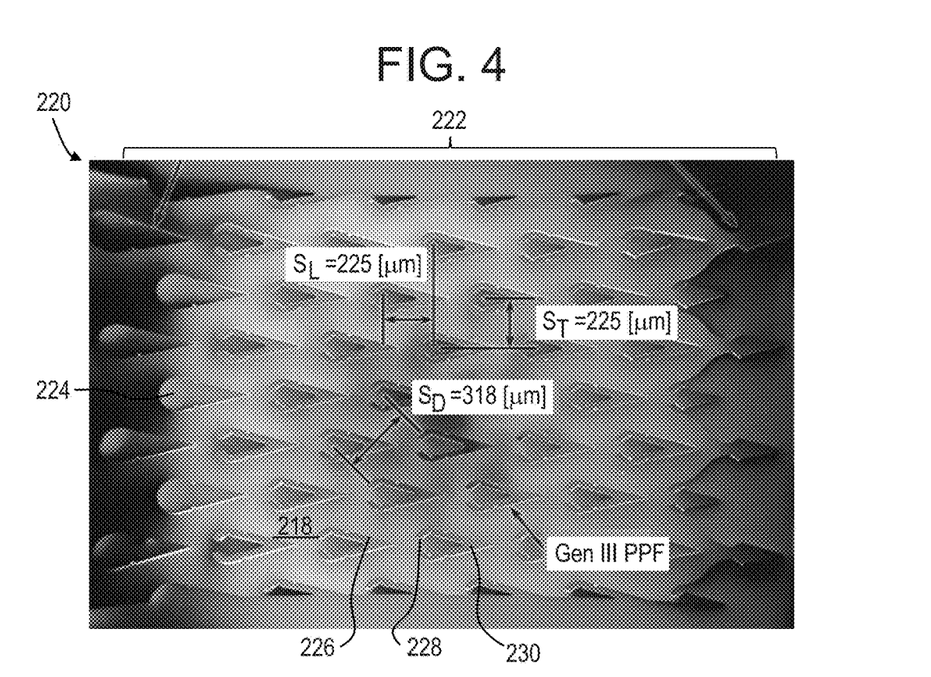
FIG. 4 is a top plan view of an array of primary fluid cooling fins according to some embodiments of the disclosed subject matter.
Figure 7:
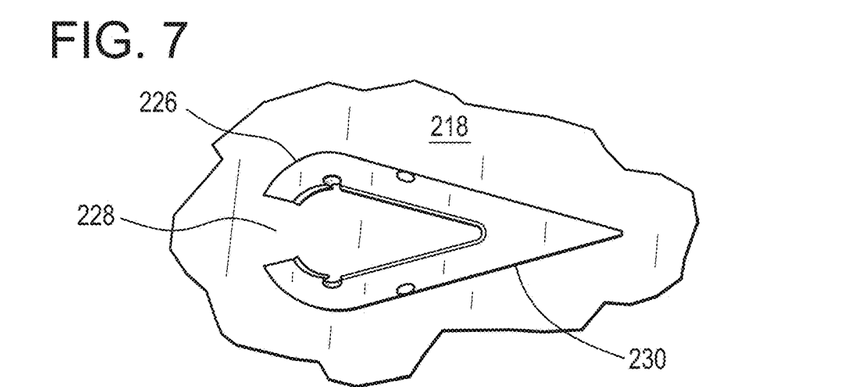
FIG. 7 is an enlarged top plan view of a primary fluid cooling fin according to some embodiments of the disclosed subject matter.

First substrate 208 includes first and second surfaces 214 and 216, respectively. First surface 214 is in thermal contact with electronic component 102. A primary channel 218 is formed in second surface 216 of first substrate 208. Primary channel 218 is configured to direct cooling fluid 104 and 104' for cooling electronic component 102 through heat sink 206. As best shown in FIG. 4, an array 220 of primary cooling fluid fins 222 is positioned within primary channel 218. As best shown in FIGS. 4 and 7, array 220 of primary cooling fluid fins 222 includes upstream solid fins 224 and downstream open fins 226. As used herein, upstream and downstream are relative to pathway 212 through which cooling fluids 104 and 104' flow. Each of open fins 226 includes an upstream opening 228 and downstream sidewalls 230. As mentioned above, a cooling fluid inlet 232 is formed in primary channel 218. Primary channel 218 is substantially parallel to a plane 234, which is defined by a surface 236 of electronic component 102 that is in thermal communication with heat sink assembly 206. In some, embodiments, primary channel 218 includes a cooling fluid outlet 238 downstream of array 220 of primary cooling fluid fins 222.

Figure 3:
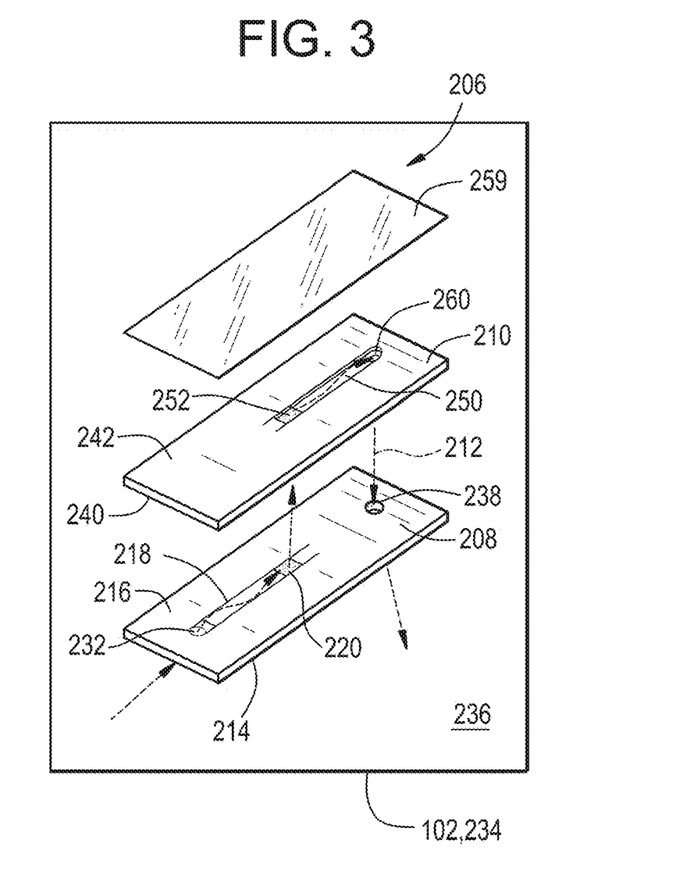
FIG. 3 is enlarged exploded isometric view of the fluid cooling assembly in FIG. 2 according to some embodiments of the disclosed subject matter.
Figure 5:
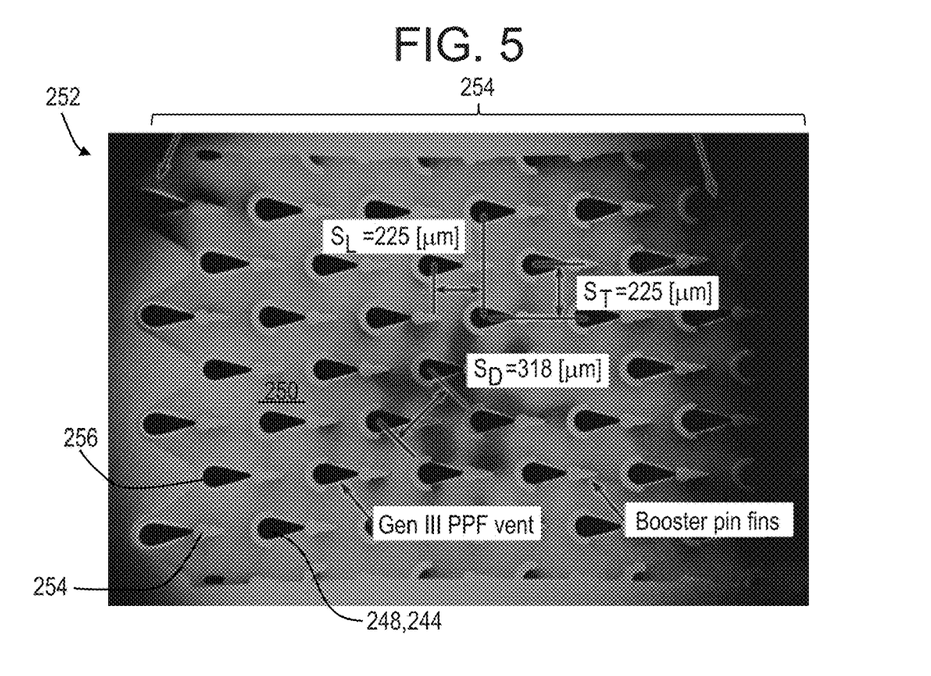
FIG. 5 is a top plan view of an array of secondary fluid cooling fins according to some embodiments of the disclosed subject matter.
Figure 6:
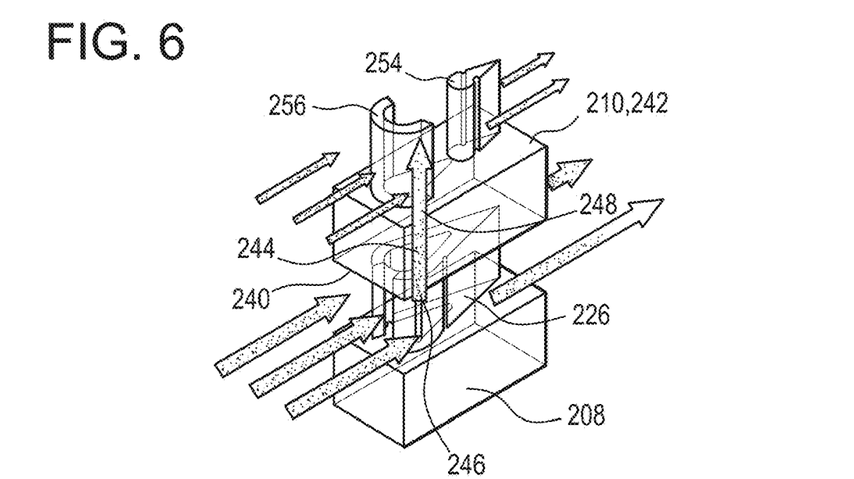
FIG. 6 is an enlarged partial isometric view of a fluid cooling assembly positioned on an electronic component according to some embodiments of the disclosed subject matter.
Figure 8:
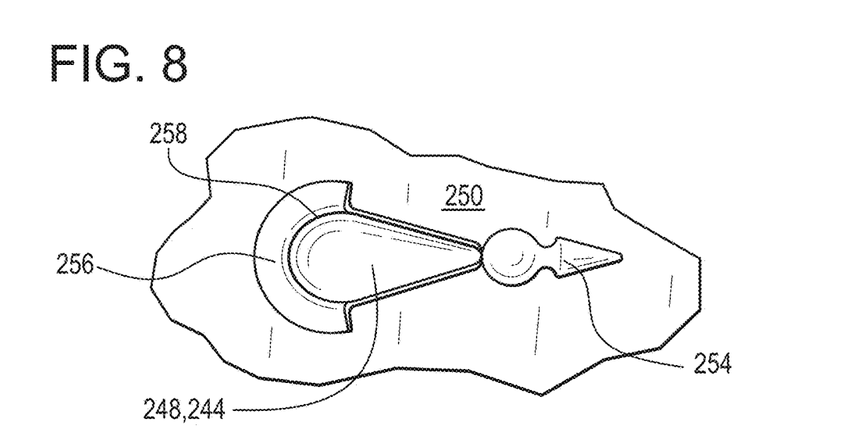
FIG. 8 is an enlarged top plan view of a secondary fluid cooling fin according to some embodiments of the disclosed subject matter.

Second substrate 210 includes first and second surfaces 240 and 242, respectively, with the first surface positioned in thermal contact with second surface 216 of first substrate 208. In some embodiments, first and second substrates 208 and 210 are joined with one another via direct fusion. Depending on the application, in some embodiments first and second substrates 208 and 210 may be bonded together by other means, e.g., welded, glued, etc., known to those skilled in the art. First and second substrates 208 and 210 are typically, but not always, formed substantially from silicon-based materials. In some embodiments, first and second substrates 208 and 210 are formed substantially of silicon carbide. In some embodiments, first and second substrates 208 and 210 are formed substantially of silicon. In some embodiments, first and second substrates 208 and 210 are formed substantially of metal. In some embodiments, first and second substrates 208 and 210 are formed substantially of copper. As best shown in FIG. 6, second substrate 210 includes cooling fluid conduits 244 that are substantially perpendicular to plane 234 defined by surface 236 of electronic component 102. Each of cooling fluid conduits 244 have upstream and downstream ends 246 and 248, respectively, that are each formed through the second substrate from the upstream end at first surface 240 to the downstream end at second surface 242. In some embodiments, primary channel 218 is configured so that substantially all of cooling fluid 104 and 104' that enters the primary channel exits the primary channel via cooling fluid conduits 244. Referring again to FIG. 3, a secondary channel 250 is formed within second surface 242 of second substrate 210. Secondary channel 250 is configured to direct partially heated cooling fluid 104' away from electronic component 102. As best shown in FIGS. 3 and 5, an array 252 of secondary cooling fluid fins 254 is positioned within secondary channel 250. Array 252 is positioned downstream of downstream end 248 of one of fluid conduits 244. As best shown in FIG. 8, each of secondary cooling fluid fins 254 includes a shroud portion 256 defined around a portion 258 of downstream end 248 of one of cooling fluid conduits 244. Shroud portion 256 is configured to prevent stagnation zones of partially heated cooling fluid 104' from forming adjacent downstream ends 248 of cooling fluid conduits 244. Secondary channel 250 is substantially parallel to plane 234 defined by surface 236 of electronic component 102.

Referring again to FIG. 3, an enclosing layer 259 is joined with second surface 242 of second substrate 210 and seals secondary channel 250. Although not necessary, in some embodiments, enclosing layer 259 is formed from a substantially transparent material such as glass, or similar. A cooling fluid outlet 260 is formed in one of enclosing layer 259 and secondary channel 250 for allowing partially heated cooling fluid 104' to exit heat sink assembly 206 via cooling outlet 238 in first substrate 208.

Figure 9:
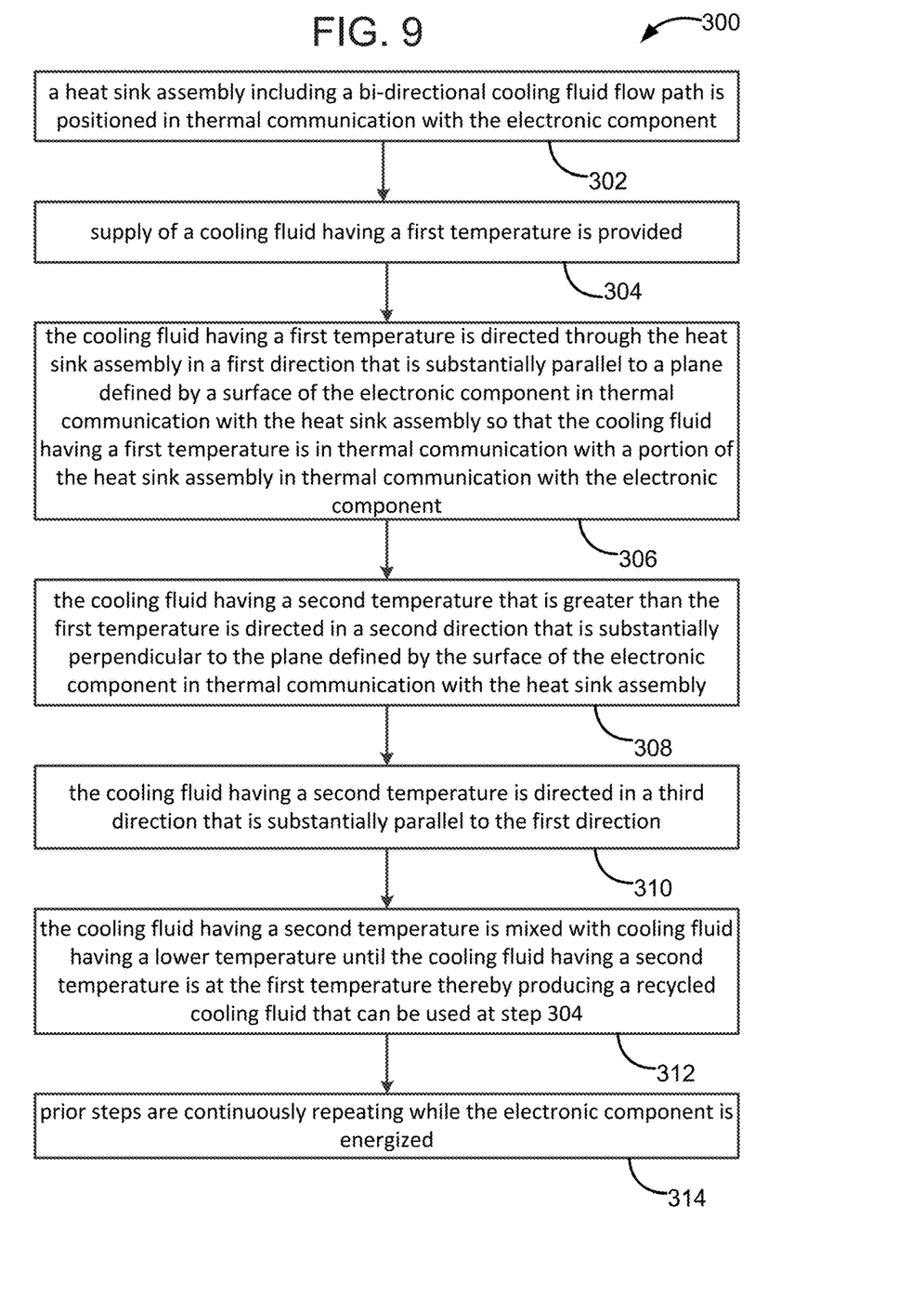
FIG. 9 is a chart of methods of cooling an electronic component according to some embodiments of the disclosed subject matter.

Referring now to FIG. 9, some embodiments of the disclosed subject matter include a method 300 of cooling an electronic component. At 302, a heat sink assembly including a bi-directional cooling fluid flow path is positioned in thermal communication with the electronic component. At 304, a supply of a cooling fluid having a first temperature is provided. At 306, the cooling fluid having a first temperature is directed through the heat sink assembly in a first direction that is substantially parallel to a plane defined by a surface of the electronic component in thermal communication with the heat sink assembly so that the cooling fluid having a first temperature is in thermal communication with a portion of the heat sink assembly in thermal communication with the electronic component. At 308, the cooling fluid having a second temperature that is greater than the first temperature is directed in a second direction that is substantially perpendicular to the plane defined by the surface of the electronic component in thermal communication with the heat sink assembly. At 310, the cooling fluid having a second temperature is directed in a third direction that is substantially parallel to the first direction. In some embodiments, at 312, the cooling fluid having a second temperature is mixed with cooling fluid having a lower temperature until the cooling fluid having a second temperature is at the first temperature thereby producing a recycled cooling fluid that can be used at step 304. In some embodiments, the cooling fluid having a lower temperature is the cooling fluid having a first temperature from the supply. In some embodiments, the cooling fluid having a lower temperature is introduced from a second supply of cooling fluid. At 314, prior steps are continuously repeating while the electronic component is energized. In some embodiments, method 300 includes providing one or more pumps for directing both the cooling fluid having a first temperature and the cooling fluid having a second temperature through the heat sink assembly.

Methods and systems according to the disclosed subject matter provide advantages and benefits over known methods and systems by being capable of dissipating ultra-high heat fluxes, e.g., from electronic components. The cooling fluid is directed to a primary substrate which communicates heat from a heat source to the cooling fluid. Primary cooling fins of the primary substrate are positioned and shaped to direct the heated cooling fluid away from the first substrate through a secondary substrate via a cooling fluid conduit, which advantageously conducts heat further away from the heat source, and improves the efficiency of the heat sink. The secondary substrate itself provides an additional heat transfer chamber, and acts to stabilize flow of cooling fluid through the system. The secondary substrate also allows inclusion of secondary cooling fins which include a shroud portion that mitigates stagnation zones as the heated cooling fluid flows around them. These features are scalable and 3D printable for simple design and fabrication for specific applications. Further, the components of the present disclosure are easily integrated and/or embedded into relatively conventional systems, e.g., transistor networks, integrated circuit networks, etc.

Although the disclosed subject matter has been described and illustrated with respect to embodiments thereof, it should be understood by those skilled in the art that features of the disclosed embodiments can be combined, rearranged, etc., to produce additional embodiments within the scope of the invention, and that various other changes, omissions, and additions may be made therein and thereto, without parting from the spirit and scope of the present invention.

What is claimed is:

1. A heat sink assembly for cooling an electronic component, said assembly comprising:
    a first substrate including first and second surfaces, said first surface being in thermal contact with said electronic component;
    a primary channel formed in said second surface of said first substrate, said primary channel being configured to direct cooling fluid for cooling said electronic component;
    an array of primary cooling fluid fins positioned within said primary channel, said array of primary cooling fluid fins including upstream solid fins and downstream open fins, wherein each downstream open fin includes an upstream opening and downstream sidewalls;
    a second substrate including first and second surfaces with said first surface of said second substrate positioned in thermal contact with said second surface of said first substrate, said second substrate including cooling fluid conduits having upstream and downstream ends and each being formed through said second substrate from said upstream end at said first surface of said second substrate to said downstream end at said second surface of said second substrate;
    a secondary channel formed within said second surface of said second substrate, said secondary channel being configured to direct partially heated cooling fluid away from said electronic component;
    an array of secondary cooling fluid fins positioned within said secondary channel, each being positioned downstream of said downstream end of one of said fluid conduits;
    an enclosing layer for sealing said secondary channel;
    a cooling fluid inlet formed in said primary channel; and
    a cooling fluid outlet formed in at least one of said enclosing layer and said secondary channel.

2. The heat sink assembly according to claim 1, wherein said first and second substrates are joined with one another via direct fusion.

3. The heat sink assembly according to claim 1, said array of secondary cooling fluid fins each including a shroud portion defined around a portion of said downstream end of one of said cooling fluid conduits, said shroud portion being configured to prevent a stagnation zone of partially heated cooling fluid from forming adjacent said downstream end of said one of said cooling fluid conduits.

4. The heat sink assembly according to claim 1, wherein said primary channel is substantially parallel to a plane defined by a surface of said electronic component in thermal communication with said heat sink assembly.

5. The heat sink assembly according to claim 4, wherein said cooling fluid conduits are substantially perpendicular to said plane defined by said surface of said electronic component.

6. The heat sink assembly according to claim 1, wherein said first and second substrate are formed substantially from silicon.

7. The heat sink assembly according to claim 1, wherein said enclosing layer is formed from a substantially transparent material.

8. The heat sink assembly according to claim 1, wherein said primary channel further comprises a cooling fluid outlet downstream of said array of primary cooling fluid fins.

9. The heat sink assembly according to claim 1, wherein said primary channel is configured so that substantially all of cooling fluid that enters said primary channel exits said primary channel via said cooling fluid conduits.

* * * * *